(12) United States Patent
Lee et al.

(10) Patent No.: US 10,695,389 B2
(45) Date of Patent: Jun. 30, 2020

(54) METHOD FOR PREPARING GINSENG POLYSACCHARIDE FOR IMMUNE STIMULATION AND GINSENG POLYSACCHARIDE FOR IMMUNE STIMULATION PREPARED THEREFROM

(71) Applicant: HEALTH BIO MAD CO., LTD., Chungcheongbuk-do (KR)

(72) Inventors: Seung Hui Lee, Seoul (KR); Gap Sun Park, Seoul (KR); Geum Hui Lee, Uiwang-si (KR)

(73) Assignee: HEALTH BIO MAD CO., LTD., Chungcheongbuk-do (KR)

( * ) Notice: Subject to any disclaimer, the term of this patent is extended or adjusted under 35 U.S.C. 154(b) by 742 days.

(21) Appl. No.: 15/313,951

(22) PCT Filed: Apr. 27, 2015

(86) PCT No.: PCT/KR2015/004155
§ 371 (c)(1),
(2) Date: Nov. 24, 2016

(87) PCT Pub. No.: WO2016/003063
PCT Pub. Date: Jan. 7, 2016

(65) Prior Publication Data
US 2017/0189464 A1 Jul. 6, 2017

(30) Foreign Application Priority Data

Jun. 30, 2014 (KR) .................... 10-2014-0081327

(51) Int. Cl.
*A61K 36/25* (2006.01)
*A61K 36/258* (2006.01)
*A61K 31/715* (2006.01)

(52) U.S. Cl.
CPC .......... *A61K 36/258* (2013.01); *A61K 31/715* (2013.01); *A61K 2236/00* (2013.01)

(58) Field of Classification Search
CPC ...................................................... A61K 36/25
USPC .......................................................... 424/728
See application file for complete search history.

(56) References Cited

U.S. PATENT DOCUMENTS 6,555,527 B1    4/2003   Yun et al.

FOREIGN PATENT DOCUMENTS

| KR | 10-0144130 B1 | 4/1998 | |
| KR | 10-2001-0050186 A | 6/2001 | |
| KR | 10-2004-0073115 A | 8/2004 | |
| KR | 100707016 B1 * | 4/2007 | ............. C08B 37/00 |
| KR | 10-0797016 B1 | 1/2008 | |
| KR | 10-2012-0000668 A | 1/2012 | |
| KR | 10-2013-0010987 A | 1/2013 | |

OTHER PUBLICATIONS

International Search Report for PCT/KR2015/004155 dated Jul. 8, 2015 from Korean Intellectual Property Office.

* cited by examiner

*Primary Examiner* — Michael Barker
*Assistant Examiner* — Deborah A Davis
(74) *Attorney, Agent, or Firm* — Revolution IP, PLLC

(57) ABSTRACT

Disclosed are a method for preparing a ginseng polysaccharide for immune stimulation and a ginseng polysaccharide for immune stimulation prepared from the preparation method, the method comprising the steps of (1) adding ingredients; (2) performing an extraction; (3) performing a first filtration and cooling; (4) performing a second filtration; (5) performing a first concentration; (6) adding a concentrate to a fermentation alcohol; (7) separating into a supernatant and a precipitate; (8) collecting the precipitate; (9) dissolving in water; (10) performing a second concentration; (11) cold ageing; (12) performing a third concentration; (13) sterilizing; and (14) packaging into a product of the ginseng polysaccharide for immune stimulation in the form of a concentrate.

9 Claims, 7 Drawing Sheets

METHOD FOR PREPARING GINSENG POLYSACCHARIDE FOR IMMUNE STIMULATION AND GINSENG POLYSACCHARIDE FOR IMMUNE STIMULATION PREPARED THEREFROM

CROSS REFERENCE TO PRIOR APPLICATIONS

This application is a National Stage Application of PCT International Patent Application No. PCT/KR2015/004155 filed on Apr. 27, 2015, under 35 U.S.C. § 371, which claims priority to Korean Patent Application No. 10-2014-0081327 filed on Jun. 30, 2014, which are all hereby incorporated by reference in their entirety.

BACKGROUND OF THE INVENTION

The present invention relates to a method for preparing a ginseng polysaccharide for immune stimulation and a ginseng polysaccharide for immune stimulation prepared therefrom, and more particularly, to a method for preparing a ginseng polysaccharide for immune stimulation that uses a ginseng polysaccharide extract containing glucose, galactose, arabinose, glucuronic acid, and galacturonic acid as active ingredients to reinforce immunity and improve control function, and a ginseng polysaccharide for immune stimulation prepared from the method.

The materials of Chinese herbal medicine, like ginseng, milk vetch root (*Astragalus membranaceus*), liriope tuber (*Liriope muscari*), etc., are recognized in their functions and widely used for the purpose of alleviation and cure of diseases. Out of the Chinese herbal medicine, ginseng (*Panax ginseng* Meyer, Araliaceae) has long been used as one of the most precious herbal medicines in Asian countries. Ginseng is the broadest concept that includes undried ginseng, white ginseng, red ginseng, wild ginseng, wood grown ginseng, tail ginseng, fresh ginseng, Taekuk ginseng, etc. The medicinal effects of ginseng are embodied in a number of medical books throughout a long history of use, and ginseng is the unchallenged health functional food in today's Korea. With the westernized dietary life, the raised standard of living and the widespread well-being concept, the current customers' preferences for food come down to diversity, high quality and health. It is therefore expected to have more demands for development of more diverse products derived from ginseng that is the representative health functional food in Korea. The general ingredients of ginseng are 50 to 70% of carbohydrates, 10 to 15% of crude protein, 3 to 8% of crude saponin, and 3 to 7% of ash, and the principal bioactive ingredients are saponin, phenols, polyacetylenes, alkaloids, polysaccharides, etc. The representative medicinal ingredient is ginseng saponin, called "ginsenoside", which is named specifically for ginseng saponin apart from other kinds of plant-derived saponins. Ginseng saponin is a glycoside consisting of glycine and aglycone portions and comes in about thirty kinds of which the structures are identified.

According to the recent studies, non-saponin portions as well as saponin portions have different medicinal actions. Therefore, such active portions are under multimodal pharmacological researches.

The non-saponin portions include essential oil, phytosterol, polyacetylenes, polyphenols, flavonoids, polysaccharides, alkaloids, vitamins, minerals, and enzymes.

The polysaccharides are classified into ginsan and panaxan. For ginsan (ginseng polysaccharide), the suffix "-an" referring to polysaccharide is added to the word "gins" of ginseng. The ginsan is a pure monosaccharide consisting of glucane (i.e., a polysaccharide of glucose monomers) and fructan (i.e., a polysaccharide of fructose monomers) and has a molecular weight of about 5,000 to 15,000, which means that the ginsan is a nanoparticle-sized polymer material. According to the results of animal experiments, the ginsan promotes the regeneration and differentiation of peripheral blood cells as well as myelocytes to accelerate hematosis and antibacterial activity and reduces side effects of radioactive treatments. Further, the ginsan activates macrophages to promote the production of interleukin-12 so that Th1-lymphocyte activates the production of interferon, increasing the activity of natural killer cells (also called "NK-cells") and the cell-mediated immunity of cytotoxic T lymphocytes against cancer cells. The ginsan is also reported to be effective in the treatment of diseases such as diabetes by reducing the blood glucose level. On the other hand, there are 21 types of panaxan, panaxan A to U, which are known to reduce the risk of cancer.

In the prior art regarding the ginseng polysaccharide, KR Patent Registration No. 0144130 (Apr. 15, 1998) discloses a ginseng protein polysaccharide used as a radiation protector and comprised of glucose, galactose, galacturonic acid, and protein. Yet, the ginseng protein polysaccharide of the prior art has no effect to reinforce immunity or improve control function by increasing the production and activity of immunocytes. In addition, KR Patent Laid-Open No. 10-2013-0010987 (Jan. 30, 2013) describes a method for purifying a ginseng panaxan monosaccharide having effects to reinforce immunity against cancer and promote hematogenous function, an analysis method for defining the characteristics of the purified panaxan monosaccharide, and a composition for immune stimulation to fight cancer and promotion of hematogenous function that comprises the analyzed ginseng panaxan monosaccharide. This prior art has no mention to ginsan components, such as galactose, arabinose, glucuronic acid, etc., other than a concentrated panaxan and does not describe the case in which it is applied to the human body, so that it lacks in information on the effects of the purified ginseng panaxan monosaccharide as a complementary medicine.

Although so many studies have been made on the preparation method of ginseng polysaccharides in association with the extraction method of ginseng polysaccharides, there is a lack of research on the ginseng polysaccharide comprising glucose, galactose, arabinose, glucuronic acid, and galacturonic acid and having effects to reinforce immunity and improve control function, and above all, a paucity of study with the method for analyzing a ginseng polysaccharide in association with human body. Therefore, more consistent research is necessary to solve this problem.

BRIEF SUMMARY OF THE INVENTION

The present invention is contrived to solve the problems with the prior art. It is an object of the present invention to provide a method for preparing a ginseng polysaccharide for immune stimulation that includes the steps of extraction and precipitation from ginseng to isolate an active component of ginsan (hereinafter, referred to as "ginseng polysaccharide") for enhancing immune function, and a ginseng polysaccharide for immune stimulation made by the preparation method.

The ginseng polysaccharide for immune stimulation according to the present invention to achieve the present invention may be prepared in the form of a concentrate or a powder.

In the present invention, there is provided a method for preparing a ginseng polysaccharide concentrate that comprises the steps of: (1) placing a water-rinsed fresh ginseng or white ginseng in a nonwoven fabric bag and adding the nonwoven fabric bag into a heat-cleaned extraction tank; (2) performing three cycles of hot water extraction at 70 to 80° C. for 50 to 75 hours using a purified water 4 to 8 times the weight of the fresh ginseng or white ginseng; (3) performing a first filtration using a 1 micrometer filter and cooling the filtrate of the first filtration down to 10 to 20° C.; (4) performing a second filtration using a 0.6 micrometer filter; (5) transferring the filtrate of the second filtration to an evaporator under vacuum to perform a first concentration to 30 to 35 Brix with pressure of 65 to 68 kgf/cm$^2$ at 45 to 55° C.; (6) mixing a 95% fermentation alcohol and a purified water in a precipitation-separation tank to adjust the fermentation alcohol to a concentration of 70 to %, adding the concentrate obtained from the step (5), and stirring for 30 to 60 minutes; (7) adding the substance obtained from the step (6) into a precipitation-separation tank maintained at 15 to 20° C. and performing precipitation for 10 to 15 hours to produce a supernatant liquid and a precipitate; (8) discarding the supernatant liquid of the step (7) and removing the precipitate of a saponin phase to collect a ginseng polysaccharide precipitate; (9) adding a purified water 3 to 5 times the weight of the ginseng polysaccharide precipitate of the step (8) to dissolve the precipitate in water; (10) transferring the dissolved precipitate of the step (9) to an evaporator under vacuum to perform a second concentration to 50 to 55 Brix with pressure of 65 to 68 kgf/cm$^2$ at 45 to 55° C.; (11) cold-ageing the concentrate of the step (10) at 5 to 10° C. for 2 to 3 weeks; (12) transferring the cold-aged concentrate of the step (11) to a packaging conveyor, stirring at 45 to 55° C. for 5 to 7 days and performing a third concentration to 70 to 75 Brix; (13) performing a high temperature sterilization with pressure of 1.6 to 2.1 kgf/cm$^2$ at 120 to 125° C. for 30 to 40 minutes to sterilize the concentrate of the step (12); and (14) packaging the sterilized ginseng polysaccharide concentrate of the step (13).

In one embodiment, the fermentation alcohol of the step (6) may include any one selected from the group consisting of ethanol, propanol, butanol, pentanol, and acetone. The fermentation alcohol may be 3 to 6 times the weight of the concentrate.

In the present invention, the step (6) may further include slowly adding the first concentrate of the step (5) to the fermentation alcohol adjusted to concentration of 70 to 80% by spraying in the precipitation-separation tank under agitation.

Also, the precipitation-separation tank may be equipped with a cooling water circulator and a cooling temperature adjustor to circulate and control cooling water at a predetermined water.

In the present invention, there is also provided a method for preparing a ginseng polysaccharide for immune stimulation that comprises: (12') after the cold ageing of the step (11), stirring at 45 to 55° C. for 1 to 2 days and maintaining the concentration to 50 to 55 Brix to stabilize the concentrate; and (13') sterilizing the stabilized concentrate of the step (12') at 120 to 125° C. and then powdering the concentrate into any one selected from the group consisting of freeze-dried (FD) powder, spray-dried (SD) powder, fluid-bed granulated powder, and fluid-bed coated powder.

In the present invention, there is also provided a ginseng polysaccharide for immune stimulation prepared in the form of a concentrate or a powder by the method for preparing a ginseng polysaccharide for immune stimulation.

In one embodiment, the ginseng polysaccharide for immune stimulation may comprise, as active components, 70 to 80 wt. % of glucose, 5 to 10 wt. % of galactose, 5 to 10 wt. % of arabinose, 0.1 to 0.5 wt. % of glucuronic acid, and 5 to 15 wt. % of galacturonic acid.

Further, the ginseng polysaccharide for immune stimulation may be used in any one food selected from the group consisting of functional foods, nutritional supplements, nutritions, health foods, nutraceuticals, designer foods, and food additives.

Effects of Invention

As described above, the ginseng polysaccharide of the present invention can establish the technique of separating polysaccharides highly effective in reinforcement of immunity from ginseng.

Further, the present invention can isolate active components of the ginseng polysaccharide, contributing to the increase of the income of farmers through the development and manufacture of health functional foods commercially available.

BRIEF DESCRIPTION OF THE SEVERAL VIEW OF THE DRAWING

DETAILED DESCRIPTION OF THE INVENTION

Figure 1:
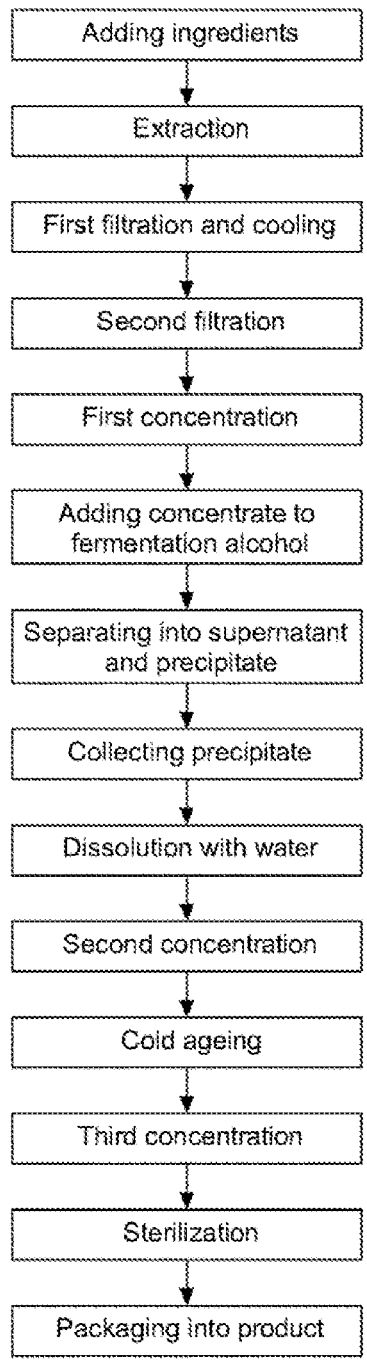
FIG. 1 is a flow chart showing a method for preparing a ginseng polysaccharide for immune stimulation according to one embodiment of the present invention.

Hereinafter, the present invention will be described in further detail with reference to the preferred embodiments in order for those skilled in the art to embody the present invention with ease. In the drawings of the present invention, the size or dimensions of the structures are illustrated to be larger or smaller than they are in reality for the clarity of the present invention, and known compositions are not shown in the drawings to illustrate specific compositions clear. In the following description of the present invention, a detailed description of known functions and configurations incorporated rein will be omitted when it may make the subject matter of the present invention rather unclear.

FIG. 1 is a flow chart showing a method for preparing a ginseng polysaccharide for immune stimulation from ginseng according to the present invention. The preparation method may comprise the steps of (1) adding ingredients; (2) performing an extraction; (3) performing a first filtration and cooling; (4) performing a second filtration; (5) performing a first concentration; (6) adding a concentrate to a fermentation alcohol; (7) separating into a supernatant and a precipitate; (8) collecting the precipitate; (9) dissolving in water; (10) performing a second concentration; (11) cold ageing; (12) performing a third concentration; (13) sterilizing; and (14) packaging into products.

More specifically, in the method for preparing a ginseng polysaccharide for immune stimulation according to the present invention, a water-rinsed fresh ginseng or white ginseng is put in a nonwoven fabric bag and added into a heat-cleaned extraction tank, in step (1). Prior to the addition of the ingredients, the extraction tank is preferably filled with purified water and heated up to 90 to 100° C. to achieve sterilization. Further, placing the fresh ginseng or white ginseng in a nonwoven fabric bag makes it easier to collect the residual of the fresh ginseng or white ginseng and prevents formation of contaminants in the concentrate.

Subsequent to the step (1), three cycles of hot water extraction is performed at 70 to 80° C. for 50 to 75 hours using a purified water 4 to 8 times the weight of the fresh ginseng or white ginseng, in the step (2). More preferably, a purified water 5 times the weight of the fresh ginseng or white ginseng is used to perform three cycles of hot water extraction at 75° C. for 20 hours per cycle. The total extraction time shorter than hours may result in the residual of the extraction undesirably small in quantity. The total extraction time longer than 75 hours is also undesirable, because the extraction process is likely to have low economic feasibility. When the extraction temperature is higher than 80° C., the thermal stability of the ginseng polysaccharide deteriorates to reduce the content of the extracted polysaccharide. When the extraction temperature is lower than 70° C., the extraction efficiency may be poor.

Subsequent to the hot water extraction step (2), a first filtration is performed using a 1 micrometer filter, and the filtrate of the first filtration is cooled down to 10 to 20° C., in the step (3). The use of the 1 micrometer filter can eliminate organic compounds, heavy metals and microorganisms possibly present in the ginseng extract. At this point, cooling down to the temperature of the defined range is effective to remove water.

Subsequent to the step (3), a second filtration is performed using a 0.6 micrometer filter, in the step (4). The use of the 0.6 micrometer filter can eliminate ginseng saponin components having a molecular weight of 800 to 1,000 and lower sugars having a molecular weight of 1,000 or less and also heavy metals and agricultural pesticides.

Subsequent to the step (4), the filtrate of the second filtration is transferred to an evaporator under vacuum to perform a first concentration to 30 to 35 Brix with pressure of 65 to 68 kgf/cm$^2$ at 45 to 55° C., in the step (5).

In the step (6), a 95% fermentation alcohol is diluted with a purified water to adjust the concentration to 70 to 80%, and the concentrate of the step (5) is slowly added to the 70-80% fermentation alcohol by spraying under agitation. Then, the mixture is stirred for 30 to 60 minutes.

In this regard, the fermentation alcohol as used herein may include any one selected from the group consisting of ethanol, propanol, butanol, pentanol, and acetone. Preferably, the fermentation alcohol is 70-95% (v/v) ethanol. The use of methanol as the fermentation alcohol is undesirable, because methanol is proved to be toxic to lymphocytes from normal mice. Further, the fermentation alcohol may be 3 to 6 times the weight of the concentrate. Preferably, the fermentation alcohol may be added in such an amount as to adjust the alcohol concentration to 70 to 80% in the total weight of the concentrate.

Then, the substance obtained from the step (6) is added into a precipitation-separation tank maintained at 15 to 20° C. and performing precipitation for 10 to 15 hours to produce a supernatant liquid and a precipitate, in the step (7). Preferably, the precipitation is performed at 18° C. for 10 hours so that the ginseng polysaccharide substance can sediment completely. The supernatant liquid thus obtained contains a large quantity of saponin, and the precipitate also contains a relatively small amount of saponin.

Subsequent to the step (7), the supernatant liquid of the step (7) is discarded, and the precipitate is removed of a saponin phase to collect a ginseng polysaccharide precipitate, in the step (8).

Upon the complete sedimentation of the ginseng polysaccharide substance, the supernatant liquid thus obtained is discarded to eliminate the saponin phase. For the removal of the saponin from the precipitate, a filter cloth or a vacuum drier is preferably available. The isolation of the ginseng polysaccharide may be performed by different methods, like filtration (including ultrafiltration, etc.), centrifugal separation, ion-exchange resin, adsorption resin, dialysis, or the like, as well as the precipitation method under agitation.

After collection of the precipitate removed of saponin in the step (8), a purified water 3 to 5 times the weight of the ginseng polysaccharide precipitate of the step (8) is used to dissolve the precipitate, in the step (9).

Subsequent to the dissolution step (9), the dissolved precipitate of the step (9) is transferred to an evaporator under vacuum to perform a second concentration to 50 to 55 Brix with pressure of 65 to 68 kgf/cm$^2$ at 45 to 55° C., in the step (10). Preferably, the concentration is performed while the internal temperature of the evaporator is not higher than 55° C. in order to concentrate to 50 to 55 Brix. Further, this step may inactivate the enzyme to achieve stabilization.

After the second concentration of the present invention, the concentrate of the step (10) is cold-aged at 5 to 10° C. for 2 to 3 weeks, in the step (11). The cold-aged concentrate of the step (11) is transferred to a packaging conveyor, stirred at 45 to 55° C. for 5 to 7 days and then subjected to a third concentration to 70 to 75 Brix, in the step (12).

Subsequently, a high temperature sterilization is performed on the concentrate of the step (12) with pressure of 1.6 to 2.1 kgf/cm$^2$ at 120 to 125° C. for 30 to 40 minutes to sterilize the concentrate, in the step (13). Finally, the sterilized ginseng polysaccharide concentrate of the step (13) is packaged into products, in the step (14).

During the packaging process, the concentrate is directly packaged into products; or the concentrate is powdered through freeze drying or hot air spray drying and then packaged into products of a predetermined capacity according to different packaging methods.

The steps subsequent to the cold ageing step (11) in the novel process of preparing a ginseng polysaccharide for immune stimulation in the form of a concentrate may be replaced by the steps of: (12') stirring at 45 to 55° C. for 1 to 2 days and maintaining the concentration to 50 to 55 Brix to stabilize the concentrate; and (13') sterilizing the stabilized concentrate of the step (12') at 120 to 125° C. and then powdering the concentrate into any one selected from the group consisting of freeze-dried (FD) powder, spray-dried (SD) powder, fluid-bed granulated powder, and fluid-bed coated powder, to prepare a ginseng polysaccharide for immune stimulation in the form of powder. The packaging process of the step (14) is the same as described in the process of preparing a ginseng polysaccharide for immune stimulation in the form of a concentrate.

In this regard, the ginseng polysaccharide for immune stimulation in the form of freeze-dried (FD) powder may be prepared in the steps of: (a) adding a purified water to the sterilized ginseng polysaccharide concentrate to dilute the concentrate to 10 to 15 Brix; and (b) adding the diluted concentrate into a freeze drier (FD) and maintaining at −40°

C. for 70 to 75 hours to collect a ginseng polysaccharide in the form of freeze-dried (FD) powder.

The ginseng polysaccharide for immune stimulation in the form of spray-dried (SD) powder may be prepared in the steps of: (a) adding a purified water to the sterilized ginseng polysaccharide concentrate to dilute the concentrate to 25 to 35 Brix; and (b) spraying the diluted concentrate through a nozzle in a spray drier (SD) air-heated at internal temperature of 140 to 190° C. to collect a ginseng polysaccharide in the form of spray-dried (SD) powder.

The ginseng polysaccharide for immune stimulation in the form of fluid-bed granulated (FBG) powder may be prepared in the steps of: (a') spraying the sterilized ginseng polysaccharide concentrate, air heating to collect a powder, and adding the powder as a nucleus into a fluid-bed granulator (FBG) maintained at 50 to 60° C.; and (b') spraying a fermentation alcohol mixed with purified water or water through spray nozzles while maintaining the temperature of the fluid-bed granulator (FBG) in the range of 50 to 60° C., and performing granulation through nucleus-nucleus coupling into particles of a desired size (16 to mesh) to collect a ginseng polysaccharide in the form of fluid-bed granulated (FBG) powder.

The ginseng polysaccharide for immune stimulation in the form of fluid-bed coated powder may be prepared in the steps of: (a") adding starch as a nucleus into a fluid-bed granulator (FBG); (b") adding a purified water to the sterilized concentrate to prepare a diluted coupling solution having 15 to 25% of a solid content; and (c") fluidizing nuclear particles while maintaining the fluid-bed granulator (FBG) at temperature of 50 to 60° C., and spraying the coupling solution through spray nozzles to coat the nuclear particles with the coupling solution into coated particles of a desired size (16 to 18 mesh) to collect a ginseng polysaccharide in the form of fluid-bed coated powder.

The present invention can prepare a ginseng polysaccharide for immune stimulation through the preparation method for a ginseng polysaccharide concentrate/powder, where the ginseng polysaccharide comprises, as active components, 70 to 80 wt. % of glucose, 5 to 10 wt. % of galactose, 5 to 10 wt. % of arabinose, 0.1 to 0.5 wt. % of glucuronic acid, and 5 to 15 wt. % of galacturonic acid.

In this regard, the polysaccharide of glucose, galactose and arabinose has the function to a sort of white blood cells, lymphocytes, which are in charge of immune function in humane body. Therefore, the ginseng polysaccharide helps the human immune system increase lymphocytes and produce macrophages and natural killer (NK) cells to fight cancer.

Further, the ginseng polysaccharide for immune stimulation as prepared in the present invention may be used in any one food selected from the group consisting of functional foods, nutritional supplements, nutritions, health foods, nutraceuticals, designer foods, and food additives. At this point, the foods to which the ginseng polysaccharide is available may include any kinds of foods, beverages, gums, teas, vitamin complexes, and health functional foods.

Hereinafter, the present invention will be described with reference to various examples, which are given to merely illustrate the present invention. It is apparent to those skilled in the present invention that the examples are not to be construed to limit the scope of the present invention.

Preparation Example 1

Preparation of Ginseng Polysaccharide Concentrate (Extraction)

Water was added to 3 kg of ginseng to perform three cycles of extraction at 80° C. At this point, the amount of water as used herein was 8 times the weight of the ginseng. The extract thus obtained was subjected to filtration and concentrated to 30 Brix.

Ethanol was added to the concentrate to sediment a ginseng polysaccharide. The supernatant liquid containing saponin was discarded, and the precipitate was removed of saponin through a filter cloth or a vacuum drier. To the isolated pure ginseng polysaccharide precipitate thus obtained was added water, which was 3 times the weight of the precipitate and used to dissolve the precipitate. The dissolved precipitate was concentrated at 50° C. to 50 Brix.

Subsequently, the concentrated ginseng polysaccharide precipitate was cold-aged at 10° C. for 2 weeks, concentrated to Brix and then sterilized at high temperature to yield a ginseng polysaccharide concentrate.

Preparation Example 2

Preparation of Ginseng Polysaccharide Powder

The procedures were performed in the same manner as described in Preparation Example 1, excepting that the cold-aged precipitate was concentrated to 55 Brix rather than 73 Brix and then freeze-dried to yield a ginseng polysaccharide powder.

Example 1: High Performance Liquid Chromatography (HPLC)

The qualitative and quantitative analysis on the sugar components constituting the ginseng polysaccharide concentrate of the present invention was performed using an HPLC (Agilent 1200 series, Agilent, USA) equipped with Eclipse XDB C18 columns.

In the HPLC analysis method, the analysis was performed six times in total for a standard solution and test solutions with variable compositions to establish the following analysis conditions.

For the HPLC analysis, a standard solution, an internal standard solution, and test solutions are prepared. The standard solution used D-(+)-galacturonic acid monohydrate, D-glucuronic acid, D-(+)-galactose, D-(+)-glucose monohydrate, and L-(+)-arabinose.

Example 1-1

20 mg of a ginseng polysaccharide concentrate was dissolved in 10 ml of purified water to prepare a standard solution. As for the internal standard solution, 10 mg of allose was dissolved in 5 ml of purified water and the resultant solution was diluted with purified water to perform a 20-fold dilution.

To prepare a testing solution, 2 ml of 2M trifluoroacetic acid (TFA) was added to 2 mg of the ginseng polysaccharide concentrate to perform hydrolysis at 110° C. for 1.5 hour under nitrogen gas atmosphere. After the hydrolysis, neutralization to pH 7.0 was performed using NaOH and HCl.

0.1 ml of the internal standard solution, 2 ml of the standard solution, and the testing solution were put into a test tube, and 0.9 ml of polymethyl pentene (PMP) and 0.9 ml of 0.3M NaOH were added. After mixing, the mixture was kept in a water bath at 70° C. to cause a reaction for 30 minutes, and 0.9 ml of 0.3M HCl was added to neutralize the mixture. Subsequently, 2 ml of chloroform was added to cause a separation/extraction from the aqueous phase. The separation/extraction process was performed three times to collect the aqueous phase, which was used for analysis.

Figure 2:
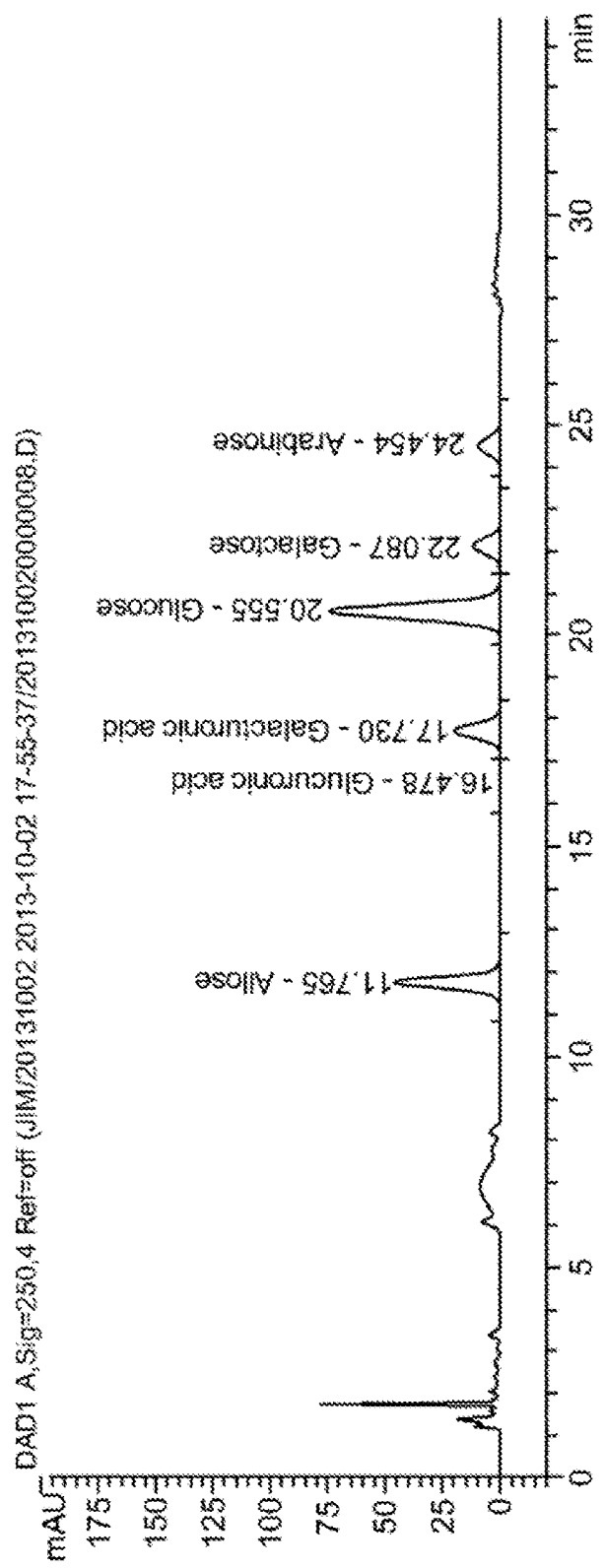
FIGS. 2 to 6 show the results of high performance liquid chromatography (HPLC) according to one embodiment of the present invention.
Figure 3:
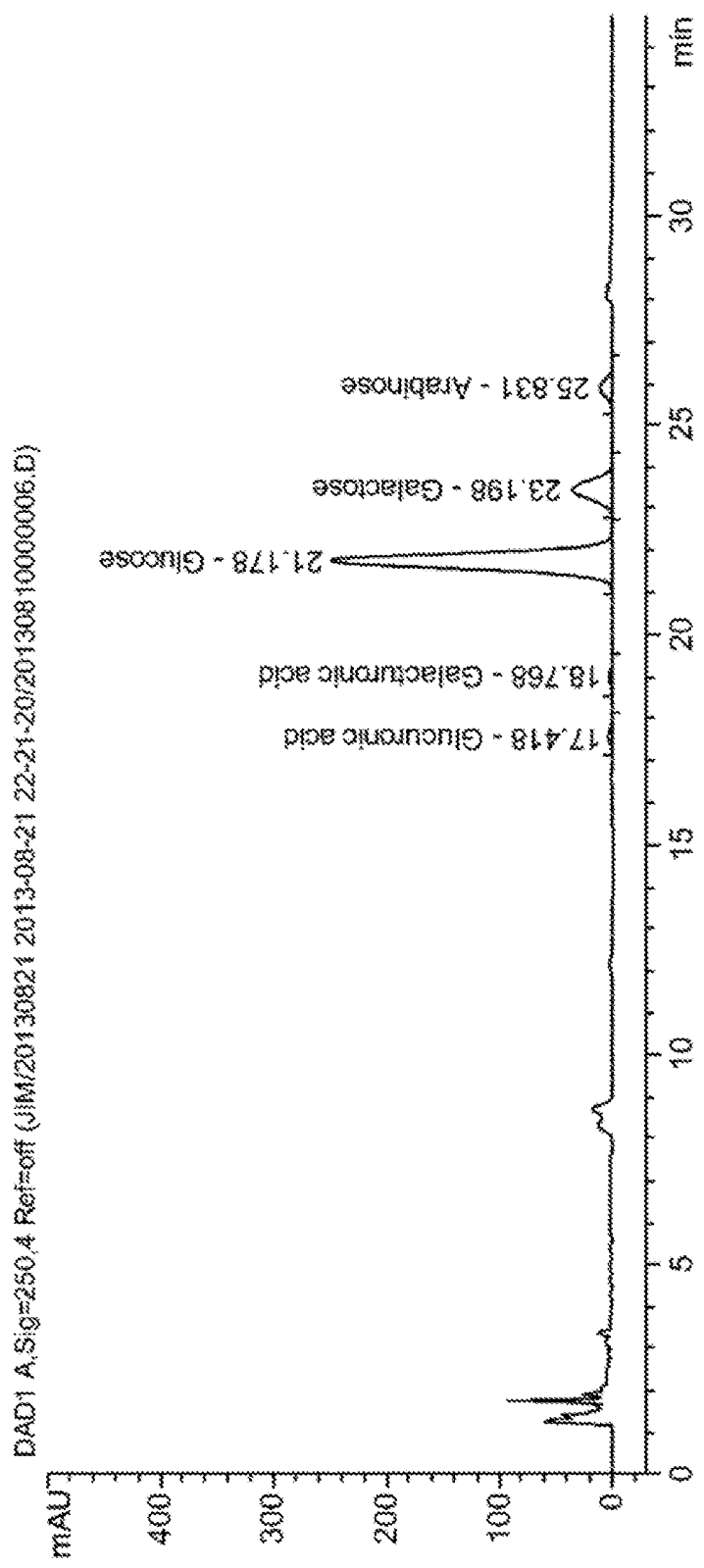
Figure 4:
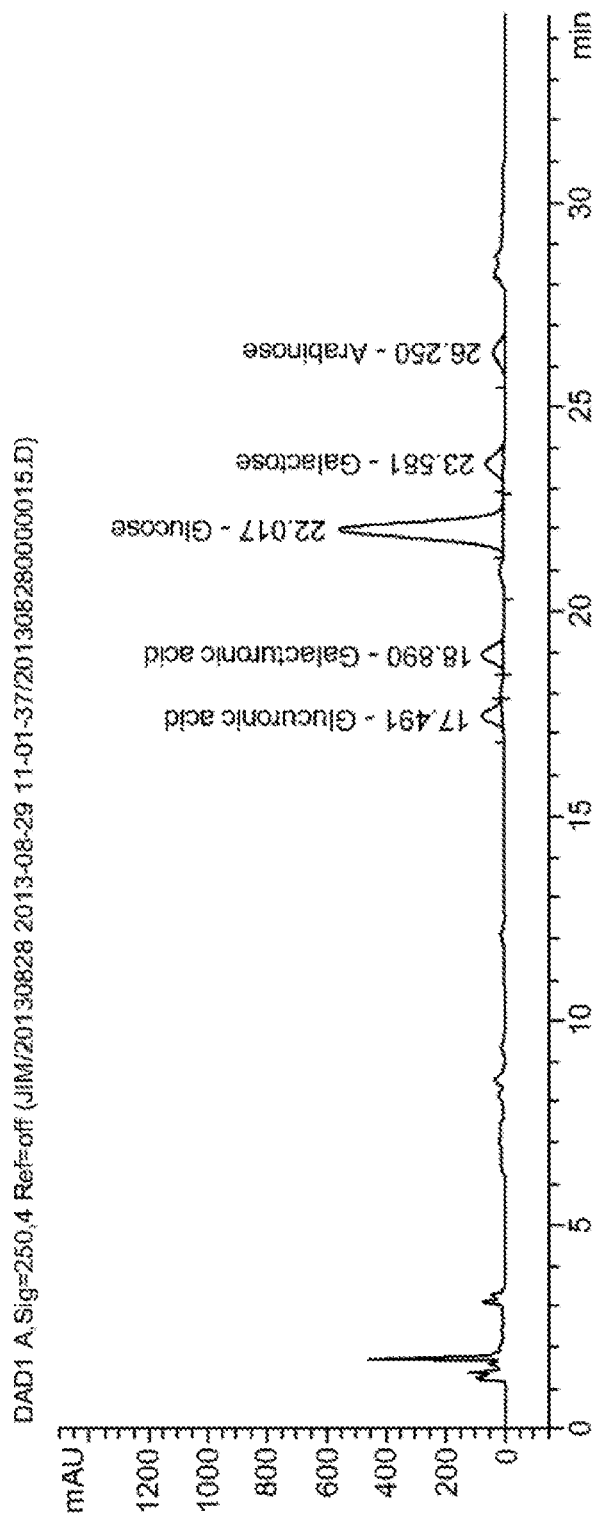
Figure 5:
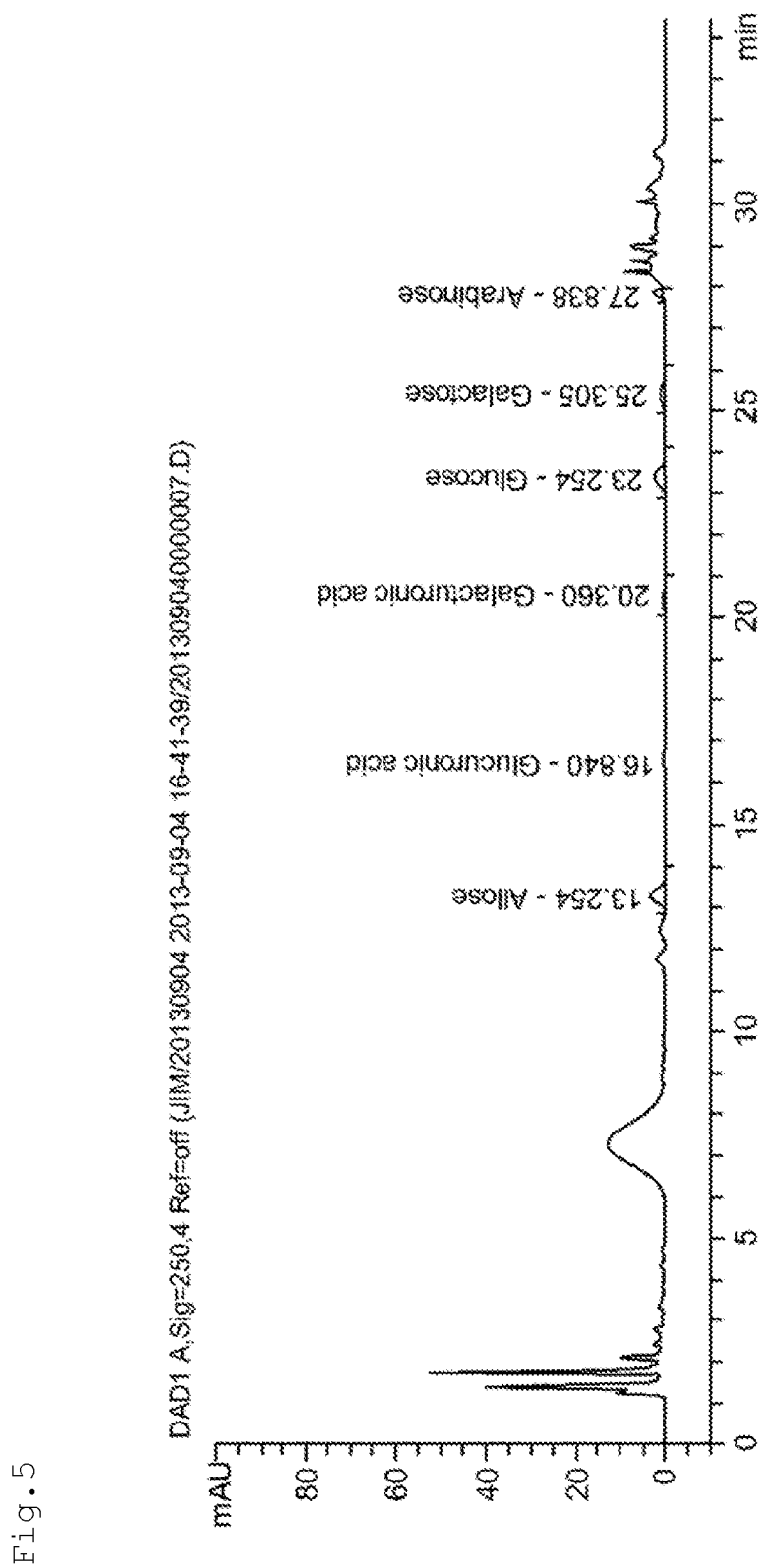

As can be seen from FIG. 2, according to the results of the analysis on the ginseng polysaccharide, peaks appeared for glucuronic acid (17.418 min), galacturonic acid (18.768 min), glucose (21.178 min), galactose (23.198 min), and arabinose (25.831 min).

Example 1-2

The procedures were performed in the same manner as described in Example 1-1, excepting that the testing solution was prepared using 1 ml of 2M TFA rather than 2 ml of 2M TFA, further adding 1 ml of 4M $H_2SO_4$ and then performing hydrolysis at 110° C. for 8 hours under nitrogen gas atmosphere and that no internal standard substance was used.

Example 1-3

The procedures were performed in the same manner as described in Example 1-1, excepting that the testing solution was prepared using 1 ml of 2M TFA rather than 2 ml of 2M TFA, adding 1 ml of 4M $H_2SO_4$ and then performing hydrolysis at 110° C. for 8 hours under nitrogen gas atmosphere; or adding 2 ml of 4M TFA and performing hydrolysis and that no internal standard substance was used.

Example 1-4

The procedures were performed in the same manner as described in Example 1-1, excepting that the testing solution was prepared using 2 ml of 4M TFA rather than 2 ml of 2M TFA and then performing hydrolysis at 110° C. for 8 hours under nitrogen gas atmosphere.

Example 1-5

The procedures were performed in the same manner as described in Example 1-1, excepting that analysis was performed at 110° C. for 8 hours rather than 1.5 hour under nitrogen gas atmosphere and that 0.45 ml of polymethylene pentene (PMP) and 0.45 ml of 0.3M NaOH were used rather than 0.9 ml of polymethyl pentene (PMP) and 0.9 ml of 0.3M NaOH.

Example 1-6

The procedures were performed in the same manner as described in Example 1-1, excepting that analysis was performed at 110° C. for 8 hours rather than 1.5 hour under nitrogen gas atmosphere.

TABLE 1

| | Retention time (RT, min) Example | | | | | |
|---|---|---|---|---|---|---|
| | 1-1 | 1-2 | 1-3 | 1-4 | 1-5 | 1-6 |
| Glucose | 20.55 | 21.17 | 22.01 | 23.25 | — | 22.34 |
| Galactose | 22.08 | 23.19 | 23.58 | 25.30 | — | |
| Arabinose | 24.45 | 25.83 | 26.25 | 27.83 | — | |
| Glucuronic acid | 16.47 | 18.76 | 18.89 | 16.84 | — | |
| Galacturonic acid | 17.73 | 17.41 | 17.49 | 20.36 | — | |

Figure 6:
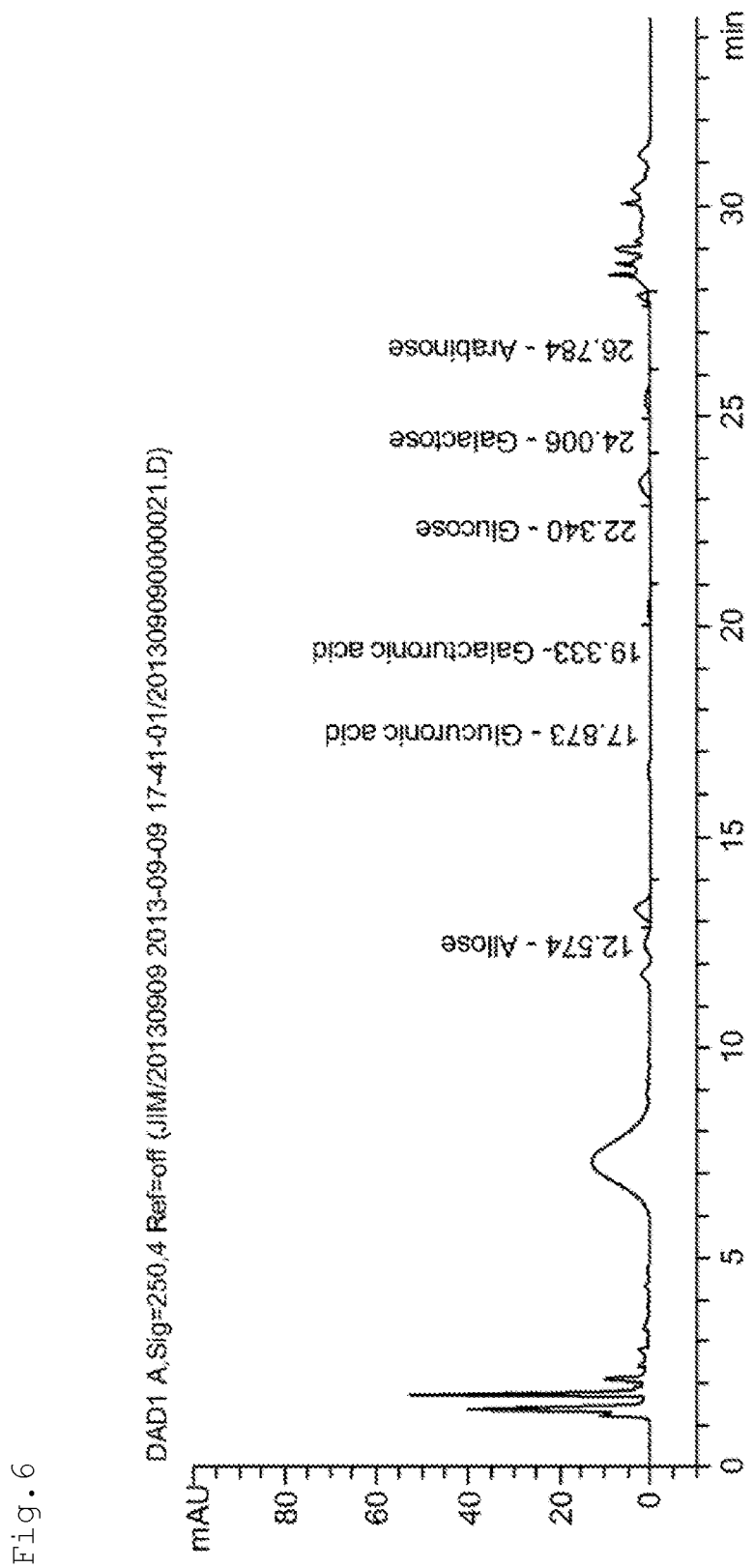

Table 1 presents the retention time of each peak for the ginseng polysaccharides of Examples 1-1 to 1-6. The quantitative analysis for each peak was achieved by determining the area of the peaks shown in FIG. 2. FIGS. 2 to 5 display GCs for Examples 1-1 to 1-4, and FIG. 6 shows GC for Example 1-6.

Example 2: Chemical Properties of Active Components

In order to determine the chemical properties of the active components, the ginseng polysaccharide extract was subjected to Sephacryl S-500 HR chromatography to obtain six fractions (G-1 to G-6). The fraction G-1 was subjected to DEAE Sephadex A-25 chromatography to obtain seven fractions (G1-1 to G1-7). Table 3 presents the sugar compositions of the ginseng polysaccharide (hereinafter, referred to as "Y-75" in Tables 3, 4 and 5) prepared by extraction and fractions G-1 and G1-1 having the highest sugar content.

TABLE 2

| | Glucose | Galactose | Arabinose | Others |
|---|---|---|---|---|
| Y-75 | 78.7 | 16.0 | 2.0 | 3.3 |
| G-1 | 84.2 | 11.7 | 2.2 | 1.9 |
| G1-1 | 91.7 | 5.8 | 0.6 | 1.9 |

Example 2-1: Proliferative Activity of Lymphocytes

Lymphocytes isolated from blood were cultivated together with ConA (concanvalin A, Sigma) or a specimen. In two days after the cultivation, the proliferative activity of lymphocytes was measured by the $^3$H-thymidine (TdR) uptake method. The results are presented in Table 3.

As can be seen from Table 4, the measurements were performed while the ginsan content of mouse spleen cells (hereinafter, referred to as "SC") was varied. As a result, the use of ginsan ends up with the high proliferative activity of the mouse spleen cells, and the G1-1 fraction displayed a relatively high proliferative activity of lymphocytes.

TABLE 3

| Culture | Dose (µg/ml) | 3H-Thymidine Incorporation (cpm) |
|---|---|---|
| SC | — | 2.443 ± 198 |
| SC + ConA | 2.5 | 211,591 ± 12,311 |
| SC + LPS | 10 | 74,942 ± 8,908 |
| SC + 75% EtOH | 1000 | 110,123 ± 7,021 |
| Inner part | 500 | 84,582 ± 6,665 |
| | 250 | 81,175 ± 5,687 |
| | 125 | 77,820 ± 4,560 |
| | 62.5 | 66,139 ± 2,235 |
| | 31.3 | 59,074 ± 4,562 |
| SC + G-1 | 1000 | 141,374 ± 10,346 |
| | 500 | 113,786 ± 11,120 |
| | 250 | 106,102 ± 8,800 |
| | 125 | 93,231 ± 9,925 |
| | 62.5 | 79,603 ± 7,580 |
| | 31.3 | 64,218 ± 9,256 |
| SC + G1-1 | 1000 | 151,078 ± 10,213 |
| | 500 | 125,534 ± 9,001 |
| | 250 | 106,225 ± 8,948 |
| | 125 | 94,750 ± 5,658 |
| | 62.5 | 83,960 ± 5,658 |
| | 31.3 | 74,541 ± 3,431 |

Example 2-2: Productive Activity of BAK Cells

Evaluations on the BAK cell productive activity and the activity to kill cancer cells were performed using the $^{51}$Cr glass method for 4 hours. The evaluation results are presented in Table 4. As a result, the spleen cells cultivated in a medium containing ginsan showed the higher activity to kill cancer than the spleen cells cultivated in a medium destitute of ginsan, and the G-1 fraction had relatively high levels of evaluation.

TABLE 4

| Culture | Dose (μg/ml) | % Cytotoxicity (Effector:Target) | |
|---|---|---|---|
| | | 100:1 | 30:1 |
| SC | — | 1.65 | 0.37 |
| SC + rIL-2 | 30 | 71.11 | 51.46 |
| SC + OK432 | 100 | 6.45 | 2.44 |
| | 50 | 14.42 | 3.93 |
| | 10 | 3.24 | 1.01 |
| SC + 75% EtOH | 200 | 16.21 | 5.14 |
| Inner part | 100 | 18.46 | 9.00 |
| | 50 | 7.71 | 2.64 |
| | 10 | 3.34 | 1.85 |
| SC + G-1 | 200 | 3.57 | 2.07 |
| | 100 | 6.89 | 2.13 |
| | 50 | 12.14 | 6.10 |
| | 10 | 19.34 | 7.91 |
| | 2 | 7.57 | 2.34 |
| SC + G1-1 | 200 | 4.46 | 1.82 |
| | 100 | 5.05 | 2.61 |
| | 50 | 19.82 | 7.61 |
| | 10 | 22.25 | 9.75 |
| | 2 | 9.56 | 3.55 |

Example 3: Human Experimentation

A human experiment was performed to evaluate the immunostimulatory activity of the ginseng polysaccharide (Y-75), and 12 immune-related vulnerable volunteers (normal old people) were recruited to participate in a test for the evaluation of the immunostimulatory activity. In this regard, the human experiment was performed using a test product containing 1 g of the extracted ginseng polysaccharide (Y-75) and 1 g of starch and a control product containing 1 g of caramel syrup and 1 g of starch.

The test volunteers were divided into four groups: a 3-volunteer group taking the control product; a 3-volunteer group taking the ginseng polysaccharide (Y-75) at a dose of 2 g/day; a 3-volunteer group taking the ginseng polysaccharide (Y-75) at a dose of 6 g/day; and a 3-volunteer group taking the ginseng polysaccharide (Y-75) at a dose of 12 g/day. The volunteers were observed in regards to change over eight weeks. At this time, the test product and the control product were orally administered twice a day, at a fixed time of 8 a.m. and 8 p.m., for 8 weeks. Blood was taken from each volunteer before the administration of the test product and the control product, and 4 weeks and 8 weeks after the administration to perform the hematologic examination and the blood chemical test.

Table 5 presents the phagocytic activity from the administration of the ginseng polysaccharide (Y-75).

TABLE 5

| | 0 g | 2 g | 6 g | 12 g |
|---|---|---|---|---|
| Before administration | 34.4 | 46.6 | 37.2 | 37.5 |
| 4 weeks after administration | 38.7 | 48.6 | 46.0 | 46.5 |
| 8 weeks after administration | 39.3 | 58.3 | 70.0 | 52.4 |

As can be seen from Table 5, the phagocytic activity increased with an increase in the number of administration days of the ginseng polysaccharide. Particularly, the phagocytic activity increased most highly when 6 g of the ginseng polysaccharide was administered.

Figure 7:
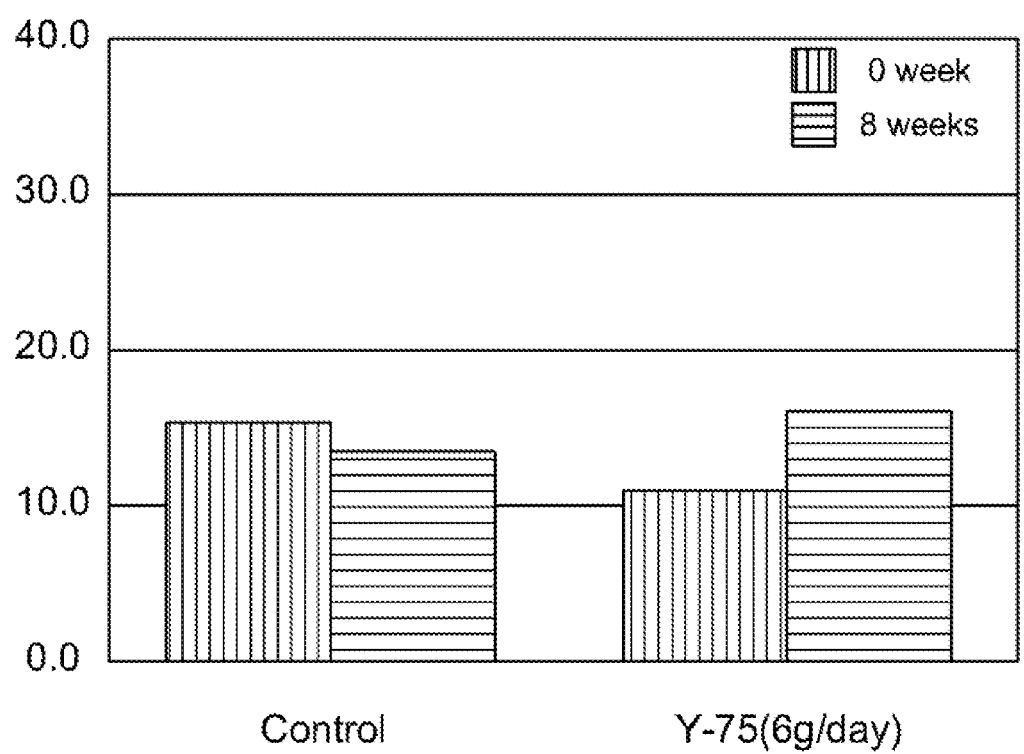
FIG. 7 shows the NK cells activity of the active components of the ginseng polysaccharide according to one embodiment of the present invention.

FIG. 7 shows the NK cell activity in the control group taking the control product and the NK cell activity aided by the active components of the ginseng polysaccharide (Y-75) in the Y-75 group taking 6 g of the ginseng polysaccharide. As a result, the NK cell activity increased with an increase in the administered amount of the active components of the ginseng polysaccharide.

According to the present invention, the method for preparing a ginseng polysaccharide that includes the step of ginseng extraction, filtration and concentration, and the components of the ginseng polysaccharide, that is, glucose, galactose, arabinose, glucuronic acid, and galacturonic acid can make effects to improve the immunostimulatory activity and the control function. In addition, the commercialization of the health functional products using the active components of the ginseng polysaccharide can contribute to the increase of the income of farmers.

Although the preferred embodiments of the present invention have been described in detail, it is understood that the present invention should not be limited to these exemplary embodiments but various alternatives can be made by those skilled in the art within the spirit and scope of the present invention as hereinafter claimed.

What is claimed is:

1. A method for preparing a ginseng polysaccharide for immune stimulation, consisting of:
   (1) placing a water-rinsed fresh ginseng or white ginseng in a nonwoven fabric bag and adding the nonwoven fabric bag into a heat-cleaned extraction tank;
   (2) performing three cycles of hot water extraction at 70 to 80° C. for 50 to 75 hours using a purified water 4 to 8 times the weight of the fresh ginseng or white ginseng;
   (3) performing a first filtration using a 1 micrometer filter and cooling the filtrate of the first filtration down to 10 to 20° C.;
   (4) performing a second filtration using a 0.6 micrometer filter;
   (5) transferring the filtrate of the second filtration to an evaporator under vacuum to perform a first concentration to 30 to 35 Brix with pressure of 65 to 68 kgf/cm2 at 45 to 55° C.;
   (6) mixing a 95% fermentation alcohol and a purified water in a precipitation-separation tank to adjust the fermentation alcohol to a concentration of 70 to 80%, adding the concentrate obtained from the step (5), and stirring for 30 to 60 minutes;
   (7) adding the substance obtained from the step (6) into a precipitation-separation tank maintained at 15 to 20° C. and performing precipitation for 10 to 15 hours to produce a supernatant liquid and a precipitate;
   (8) discarding the supernatant liquid of the step (7) and removing the precipitate of a saponin phase to collect a ginseng polysaccharide precipitate;

(9) adding a purified water 3 to 5 times the weight of the ginseng polysaccharide precipitate of the step (8) to dissolve the precipitate in water;
(10) transferring the dissolved precipitate of the step (9) to an evaporator under vacuum to perform a second concentration to 50 to 55 Brix with pressure of 65 to 68 kgf/cm2 at 45 to 55° C.;
(11) cold-ageing the concentrate of the step (10) at 5 to 10° C. for 2 to 3 weeks;
(12) transferring the cold-aged concentrate of the step (11) to a packaging conveyor, stirring at 45 to 55° C. for 5 to 7 days and performing a third concentration to 70 to 75 Brix;
(13) performing a high temperature sterilization with pressure of 1.6 to 2.1 kgf/cm2 at 120 to 125° C. for 30 to 40 minutes to sterilize the concentrate of the step (12); and the ginseng polysaccharide comprises, as active components, 70 to 80 wt. % of glucose, 5 to 10 wt % of galactose, 5 to 10 wt % of arabinose, 0.1 to 0.5 wt % of glucuronic acid, and 5 to 15 wt % of galacturonic acid; and
(14) packaging the sterilized ginseng polysaccharide concentrate of the step (13).

2. The method as claimed in claim 1, wherein the fermentation alcohol of the step (6) includes any one selected from the group consisting of ethanol, propanol, butanol, pentanol, and acetone, wherein the fermentation alcohol is 3 to 6 times the weight of the concentrate.

3. The method as claimed in claim 1, wherein the step (6) further includes slowly adding the first concentrate of the step (5) to the fermentation alcohol adjusted to concentration of 70 to 80% by spraying in the precipitation-separation tank under agitation.

4. The method as claimed in claim 3, wherein the precipitation-separation tank is equipped with a cooling water circulator and a cooling temperature adjustor to circulate and control cooling water at a predetermined water.

5. A method for preparing a ginseng polysaccharide for immune stimulation, consisting of:
(1) placing a water-rinsed fresh ginseng or white ginseng in a nonwoven fabric bag and adding the nonwoven fabric bag into a heat-cleaned extraction tank;
(2) performing three cycles of hot water extraction at 70 to 80° C. for 50 to 75 hours using a purified water 4 to 8 times the weight of the fresh ginseng or white ginseng;
(3) performing a first filtration using a 1 micrometer filter and cooling the filtrate of the first filtration down to 10 to 20° C.;
(4) performing a second filtration using a 0.6 micrometer filter;
(5) transferring the filtrate of the second filtration to an evaporator under vacuum to perform a first concentration to 30 to 35 Brix with pressure of 65 to 68 kgf/cm2 at 45 to 55° C.;
(6) mixing a 95% fermentation alcohol and a purified water in a precipitation-separation tank to adjust the fermentation alcohol to a concentration of 70 to 80%, adding the concentrate obtained from the step (5), and stirring for 30 to 60 minutes;
(7) adding the substance obtained from the step (6) into a precipitation-separation tank maintained at 15 to 20° C. and performing precipitation for 10 to 15 hours to produce a supernatant liquid and a precipitate;
(8) discarding the supernatant liquid of the step (7) and removing the precipitate of a saponin phase to collect a ginseng polysaccharide precipitate;
(9) adding a purified water 3 to 5 times the weight of the ginseng polysaccharide precipitate of the step (8) to dissolve the precipitate in water;
(10) transferring the dissolved precipitate of the step (9) to an evaporator under vacuum to perform a second concentration to 50 to 55 Brix with pressure of 65 to 68 kgf/cm2 at 45 to 55° C.;
(11) cold-ageing the concentrate of the step (10) at 5 to 10° C. for 2 to 3 weeks;
(12') stirring the cold ageing concentrate at 45 to 55° C. for 1 to 2 days and maintaining the concentrate to 50 to 55 Brix to stabilize the concentrate; and
(13') sterilizing the stabilized concentrate of the step (12') at 120 to 125° C. and then powdering the concentrate into any one selected from the group consisting of freeze-dried (FD) powder, spray-dried (SD) powder, fluid-bed granulated powder, and fluid-bed coated powder, wherein the ginseng polysaccharide comprises, as active components, 70 to 80 wt. % of glucose, 5 to 10 wt. % of galactose, 5 to 10 wt. % of arabinose, 0.1 to 0.5 wt. % of glucuronic acid, and 5 to 15 wt. % of galacturonic acid.

6. The method as claimed in claim 5, wherein the powdering step (13') comprises:
(a) adding a purified water to the sterilized ginseng polysaccharide concentrate to dilute the concentrate to 10 to 15 Brix; and
(b) adding the diluted concentrate into a freeze drier and maintaining at −40° C. for 70 to 75 hours to collect a ginseng polysaccharide in the form of freeze-dried powder.

7. The method as claimed in claim 5, wherein the powdering step (13') comprises:
(a) adding a purified water to the sterilized ginseng polysaccharide concentrate to dilute the concentrate to 25 to 35 Brix; and
(b) spraying the diluted concentrate through a nozzle in a spray drier (SD) air-heated at internal temperature of 140 to 190° C. to collect a ginseng polysaccharide in the form of spray-dried powder.

8. The method as claimed in claim 5, wherein the powdering step (13') comprises:
(a') spraying the sterilized ginseng polysaccharide concentrate, air heating to collect a powder, and adding the powder as a nucleus into a fluid-bed granulator (FBG) maintained at 50 to 60° C.; and
(b') spraying a fermentation alcohol mixed with purified water or water through spray nozzles while maintaining the temperature of the fluid-bed granulator (FBG) in the range of 50 to 60° C., and performing granulation through nucleus-nucleus coupling into particles of a desired size (16 to 18 mesh) to collect a ginseng polysaccharide in the form of fluid-bed granulated (FBG) powder.

9. The method as claimed in claim 5, wherein the powdering step (13') comprises:
(a") adding starch as a nucleus into a fluid-bed granulator (FBG);
(b") adding a purified water to the sterilized concentrate to prepare a diluted coupling solution having 15 to 25% of a solid content; and
(c") fluidizing nuclear particles while maintaining the fluid-bed granulator (FBG) at temperature of 50 to 60° C., and spraying the coupling solution through spray nozzles to coat the nuclear particles with the coupling solution into coated particles of a desired size (16 to 18 mesh) to collect a ginseng polysaccharide in the form of fluid-bed coated powder.

\* \* \* \* \*